(12) United States Patent
Stainvas Olshansky et al.

(10) Patent No.: US 9,453,941 B2
(45) Date of Patent: Sep. 27, 2016

(54) ROAD SURFACE REFLECTIVITY DETECTION BY LIDAR SENSOR

(71) Applicant: GM GLOBAL TECHNOLOGY OPERATIONS LLC, Detroit, MI (US)

(72) Inventors: Inna Stainvas Olshansky, Modiin (IL); Yosi Buda, Petach-Tikya (IL); Ariel Lipson, Tel Aviv (IL)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 29 days.

(21) Appl. No.: 14/578,638

(22) Filed: Dec. 22, 2014

(65) Prior Publication Data
US 2016/0178802 A1 Jun. 23, 2016

(51) Int. Cl.
*G01N 21/55* (2014.01)
*B60W 40/06* (2012.01)
*G01W 1/10* (2006.01)
*G01N 21/49* (2006.01)
*B60W 40/068* (2012.01)

(52) U.S. Cl.
CPC ............... *G01W 1/10* (2013.01); *G01N 21/49* (2013.01); *G01N 21/55* (2013.01); *B60W 40/06* (2013.01); *B60W 40/068* (2013.01); *G01N 2021/556* (2013.01); *G01N 2201/125* (2013.01)

(58) Field of Classification Search
CPC ........... G01W 1/10; G01N 2021/556; G01N 2021/125; G01N 21/49; G01N 21/55; B60W 40/06; B60W 40/068; G05D 2201/0213
USPC .......... 356/600–604, 341, 4.01, 4.1; 701/17, 701/200, 213, 208, 301, 428
See application file for complete search history.

(56) References Cited

U.S. PATENT DOCUMENTS

| | | | | |
|---|---|---|---|---|
| 4,781,465 A * | 11/1988 | Demachi | ............ | B60G 17/0165 356/3.07 |
| 4,985,847 A * | 1/1991 | Shioya | ............ | G01C 3/10 250/202 |
| 5,181,258 A * | 1/1993 | Nagao | ............ | G06K 9/4647 348/130 |
| 6,166,645 A * | 12/2000 | Blaney | ............ | G08B 19/02 250/339.11 |
| 8,825,260 B1 * | 9/2014 | Silver | ............ | G01S 17/936 342/118 |
| 8,941,739 B2 * | 1/2015 | Yoo | ............ | G01S 17/88 348/148 |
| 9,139,204 B1 * | 9/2015 | Zhao | ............ | G01C 21/00 |
| 2006/0261975 A1 * | 11/2006 | Fridthjof | ............ | B60T 8/172 340/905 |
| 2007/0276599 A1 * | 11/2007 | Ogawa | ............ | G06K 9/4604 382/181 |
| 2009/0097038 A1 * | 4/2009 | Higgins-Luthman | | B60G 17/019 356/602 |
| 2010/0019964 A1 * | 1/2010 | Huang | ............ | G01M 17/06 342/357.31 |
| 2010/0098295 A1 * | 4/2010 | Zhang | ............ | G06K 9/00798 382/103 |
| 2010/0114416 A1 * | 5/2010 | Au | ............ | G01C 21/165 701/23 |
| 2012/0330513 A1 * | 12/2012 | Charnesky | ............ | B62D 35/005 701/48 |
| 2013/0100438 A1 * | 4/2013 | Breuer | ............ | G01P 13/00 356/51 |
| 2014/0307247 A1 * | 10/2014 | Zhu | ............ | G01S 17/023 356/4.01 |
| 2014/0336842 A1 * | 11/2014 | Jang | ............ | G06K 9/00805 701/1 |

* cited by examiner

*Primary Examiner* — Sang Nguyen (57) ABSTRACT

A method of determining a surface condition of a road of travel. A light beam directed at a surface in the road of travel is transmitted utilizing a lidar system. A response is analyzed at a photodetector of the lidar system after transmitting the light beam. A determination is made whether a form of precipitation is present on the road of travel in response to analyzing the response at the photodetector. A precipitation indicating signal is generated in response to the determination that the ground surface includes a form of precipitation on the road of travel.

20 Claims, 8 Drawing Sheets

ROAD SURFACE REFLECTIVITY DETECTION BY LIDAR SENSOR

BACKGROUND OF INVENTION

An embodiment relates to a determination of road surface condition reflectivity of a traveled route.

Understanding the road surface conditions that a vehicle is encountering is very important for various functionality of a vehicle. Precipitation on the road surface may result in various control issues for the vehicle. Snow, water, or ice on the road of travel greatly reduces the coefficient of friction between the vehicle tires and the surface of the road resulting in vehicle stability issues. Various known systems can sense such a condition, but require a stimulus for the detection. For example, a system that senses precipitation on the road utilizing wheel slip may detect when the vehicle wheels have sudden increases in the speed of rotation of the wheel. While this operation is very good for identifying some type of precipitation on the road surface, the issue is the precipitation is already negatively impacting the vehicle operation. As a result, the vehicle must reactively make changes to the vehicle operation to reduce the effects of the precipitation already affecting the vehicle.

Identifying a road surface condition prior to the vehicle traveling on the precipitation allows a vehicle to proactively enable various safety driving features of a vehicle or make changes to the current vehicle operations to reduce the changes of the precipitation affecting the operations of the vehicle.

SUMMARY OF INVENTION

An advantage of an embodiment is the detection of a road surface condition which allows an enablement of the stability control operations to mitigate the water/snow/ice on a surface of the road. The system utilizes a lidar technique which determines whether a signal is received at a photodetector. A determination of whether the surface includes ice/snow/water on the road of travel is performed by analyzing signals received at the photodetector as well as an absence of signals received at the photodetector. Various techniques may be used to determine ice/snow/water on the surface of the surface of the road such as no response signal received, a response signal receive have an increased scattered beam as determined by analyzing the received signal using a sliding window, and detection of false objects in the return signal.

In addition, other sensing devices/systems may be used with the lidar system to enhance the probability of the road surface condition as well as the type of precipitation on the road surface.

An embodiment contemplates a method of determining a surface condition of a road of travel. A light beam directed at a surface in the road of travel is transmitted utilizing a lidar system. A response at a photodetector of the lidar system is analyzed after transmitting the light beam. A determination is made whether a form of precipitation is present on the road of travel in response to analyzing the response at the photodetector. A precipitation indicating signal is generated in response to the determination that the ground surface includes a form of precipitation on the road of travel.

DETAILED DESCRIPTION

Figure 1:
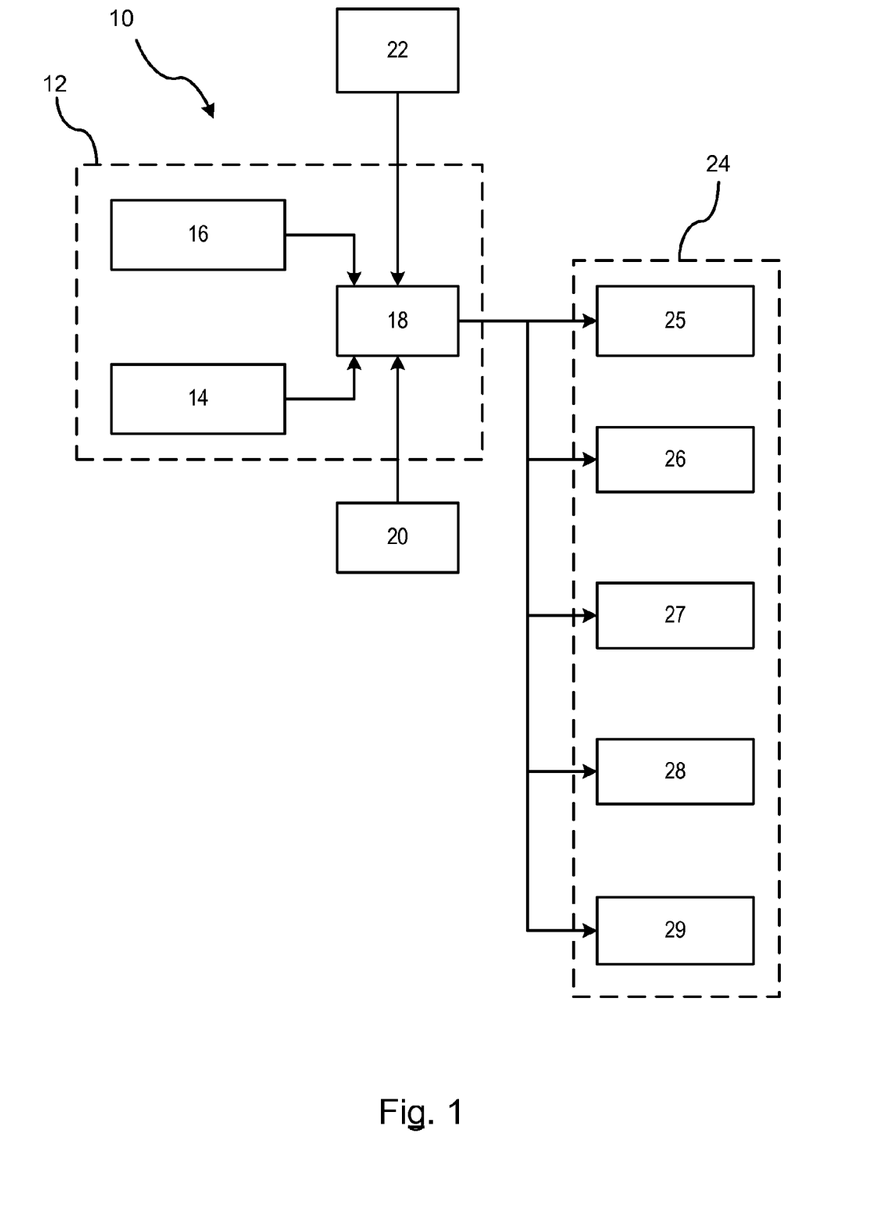
FIG. 1 is a block diagram of a road surface condition detection system.

There is shown in FIG. 1, a block diagram of the road surface condition detection system 10. The road surface detection system 10 utilizes a lidar system 12 (e.g., Velodyne sensing system). Lidar is a remote sensing technology where a target is illuminated and a distance to the object is measured based on analyzing the reflected light.

The lidar system 12 includes an illumination source 14, such a laser. Lasers are calibrated to a respective wavelength and the laser can be set at a specified pulse length and repetition rate which controls the data collection speed.

The lidar system 12 further includes a photodetector 16 receiving the reflected rays from the illumination source 14.

The lidar system 12 further includes a processor 18 for analyzing the data obtained from the photodetector 16, and for making determinations of the reflective properties of the surface condition of the road. The lidar system 12 may further utilize a positioning system/navigation system for identifying an absolute position of a surface condition if the vehicle is mobile. When a vehicle moves, lidar scans can be combined into dense point clouds (if positioning/navigation systems are available or sensors from which ego-motion can be estimated) and the same analysis can be applied for point cloud patches. This enables the lidar system to get a substantial amount of information about the road surface surrounding the vehicle.

A memory storage unit 20 may be utilized for storing information collected by the photodetector 18. The memory storage unit 20 stores data utilized by a classifier for determining the road surface which will be discussed in detail later. Other sensing devices 22 (e.g., radar, video) that can be used in combination with the lidar system to verify the condition of the road surface.

A plurality of devices devices/systems 24 may be used to enable vehicle operation to assist the driver in maintaining control of the vehicle when slick road conditions are present or provide detailed information to the driver of the vehicle that informs or warns the driver of the vehicle of the upcoming road condition. Precipitation on the vehicle road 12 can result in a reduction of traction when driving on the wet surface. It should be understood that the term precipitation as defined herein may include, but is not limited to, water, ice, snow, or other substance that can cause the vehicle to lose traction. Precipitation disposed on the vehicle road lowers the coefficient of friction between the vehicle tires and the vehicle road, thereby reducing the traction between the vehicle tires and the vehicle road. Loss of traction can be mitigated by any of the following including, but not limited to, autonomous braking controls 25 using a variable braking force to minimize the precipitation formed on the braking surfaces of the braking; components warning the driver to lower the vehicle speed to one that is conducive to the environmental conditions or notification to the driver to maintain a greater stopping distance to a lead vehicle; stability traction controls 26, speed control for deactivating or restricting the activation of cruise control functionality while precipitation is detected 27; driver warning output device to warn the driver of an upcoming road surface condition 28; or communication system for communicating to other vehicle utilizing a ad-hoc vehicle communication to forewarn other drivers of the road surface condition 29.

Figure 2:
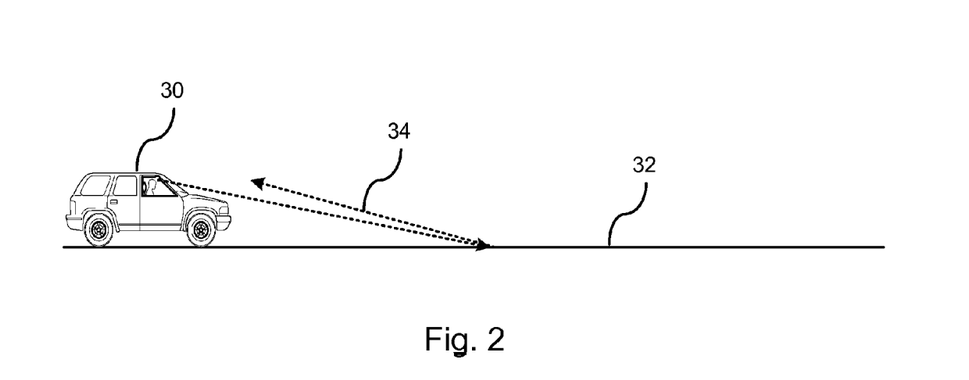
FIG. 2 is a pictorial illustration showing reflective properties for a diffused road surface.
Figure 3:
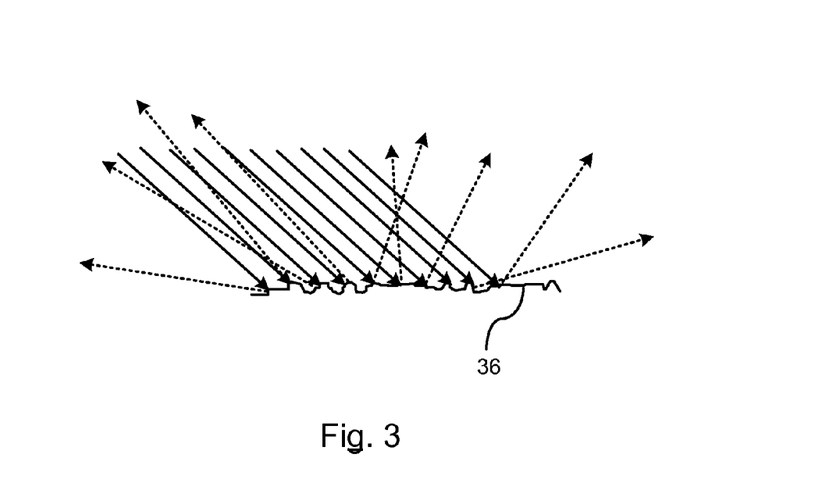
FIG. 3 an enlarged view of the diffused road surface.

There is shown in FIGS. 2 and 3, a vehicle 30 traveling along a road of travel 32 and directing a laser beam 34 at the surface of the road of travel 32. Depending on whether the road is diffused surface or a flat mirror-like surface, will determine how light rays are reflected from the surface of the road of travel 32. FIG. 3 illustrates an enhanced view of a diffused surface 36 on the road of travel 32. A diffused reflection occurs when the laser beam reflects off a surface that is not specular. Diffused reflection is the reflection of light from a surface such that an incident ray is reflected at many angles rather than at just one angle as in the case of specular reflection. As a result of incident ray being reflected at many angles as illustrated, a portion of the reflected rays return in a direction toward the vehicle. The photodetector captures the return rays and is able to measure the distance from the vehicle to the point of intersection with the diffused surface. Based on an expected return versus what is or is not received, will assist in making the determination of the road surface condition.

Figure 4:
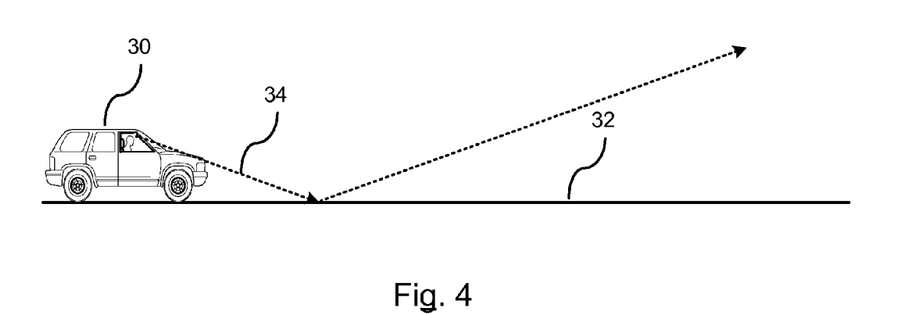
FIG. 4 is a pictorial illustration showing reflective properties for a specular road surface.
Figure 5:
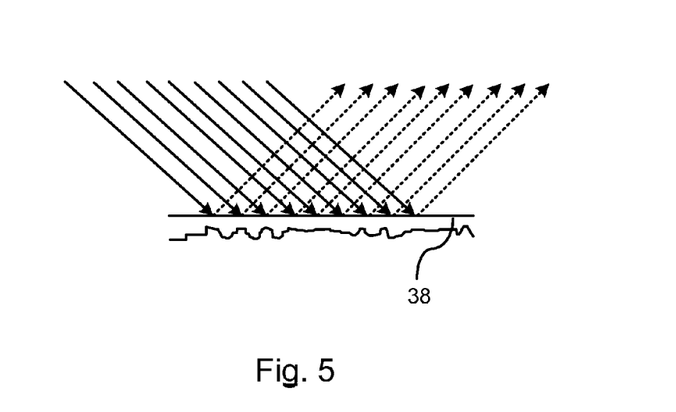
FIG. 5 is an enlarged view of the specular road surface.

FIGS. 4 and 5 illustrate the vehicle 30 traveling along the road of travel 32 and directing the laser beam 34 at the surface of the road of travel 32 where the surface is a mirror-like surface 38. A road surface having a mirror-like surface 38 will cause a specular reflection. Specular reflection is the mirror-like reflection of light from the surface where light from the incident ray coming from a single incoming direction is reflected into a single outgoing direction. As a result, the reflection ray is directed in a direction away from the vehicle since the angle of reflection is equal to the angle of incident with respect to the road surface. By identifying whether the road surface includes a diffused surface or a specular surface, decisions may be made as to mitigate the road surface condition through vehicle controls.

Vehicle control requires knowledge of the road surface condition ahead (i.e. if the road is wet, covered by ice, dry). Such conditions can be perceived utilizing the lidar systems and analyzing the data. Lidar returns, as described earlier, depend on the properties of the material from which it is reflected. The reflective properties of the road in wet/dry/snow regions differ significantly and thus can be detected using a lidar sensor. For example, during a rain, potholes in the road surface are filled with water and may behave like small mirrors. If a lidar beam hits the wet/water surfaces, the following effects can occur: (1) No returns back to the sensor detector; (2) scattering of the beam-signal reading is larger for data coming from reflective surface; (3) false objects can appear. The following descriptions herein will describe these respective effects and their analysis.

Figure 6A:
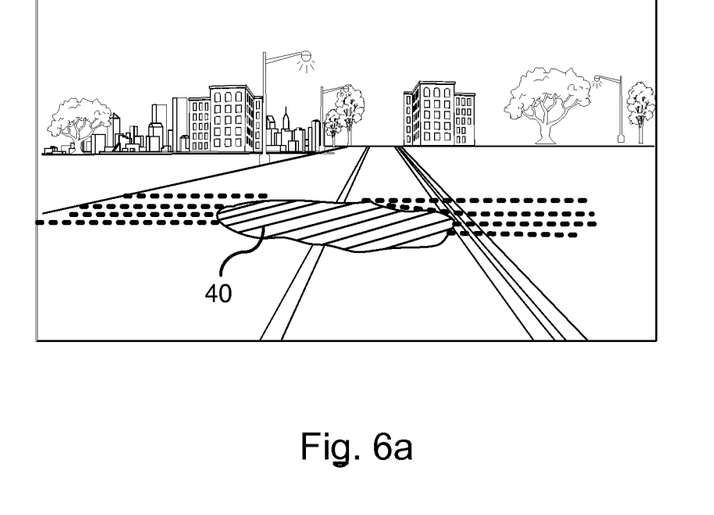
FIGS. 6a and 6b illustrate the respective lidar return signals illustrating an absence of lidar returns from the ground surface.
Figure 6B:
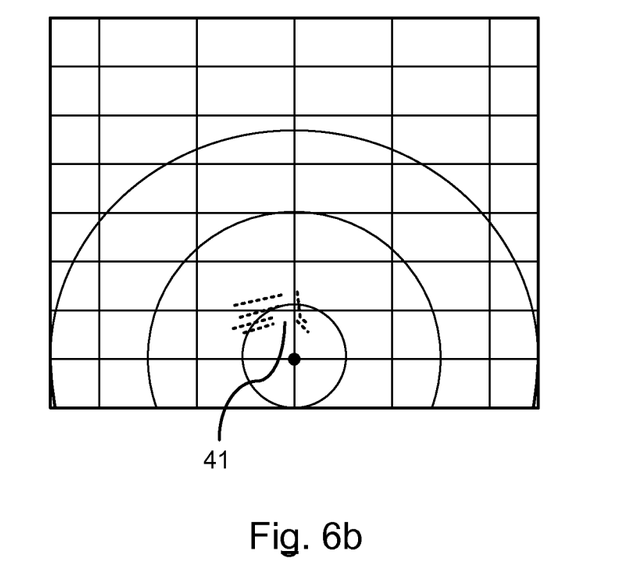

FIGS. 6*a* and 6*b* illustrate the first scenario where there is an absence of lidar returns from the ground surface, this condition can easily be detected by tracing the laser signal in time and discovering unread data where return data is expected. FIG. 6*a* illustrates lidar returns overlaid onto an image of the road of travel as seen by the driver, and FIG. 6*b* illustrates an overhead lidar return signal plot. The respective lines represent the respective laser beams that are used in a specific sensor, such as an IBEO LUX sensor. The IBEO LUX sensor has 4 layers of lasers with the vertical field of view of 3.2 degrees and scanning rate of either of 12.5 Hz, 25 Hz, and 40 Hz; however, other sensors can be utilized that have other number of laser beams. As shown in FIG. 6*a*, element 40 illustrates water on a road surface creating a mirror like surface. A void 41 indicated no return signals from the transmitted signal is shown in both FIGS. 6*a* and 6*b*. The no return signal is the result of the laser beam bouncing off the mirror like surface and reflecting forward of the vehicle. As a result, a void appears in the return lidar signal. Such a situation may occur at the curbsides where the vehicle system could include a lane centering system that looks for curbs. While detecting curbs along the road of travel, a determination is made that there are no returns for a nearby curb line that is expected to be there. Due to the design of the road, the surface of the curb has a negative curvature in the direction orthogonal to the direction of the road, which results in water pooling nearby the curb surface. As a result, the lidar beam does not return a reflection ray in certain spots and a pattern over time indicates that the pattern is broken where road and curb surfaces meet. The broken pattern indicates water or other mirror-like conditions on the surface of the road. Therefore, specular surfaces can be detected when no return signal is returned when expected.

Figure 7:
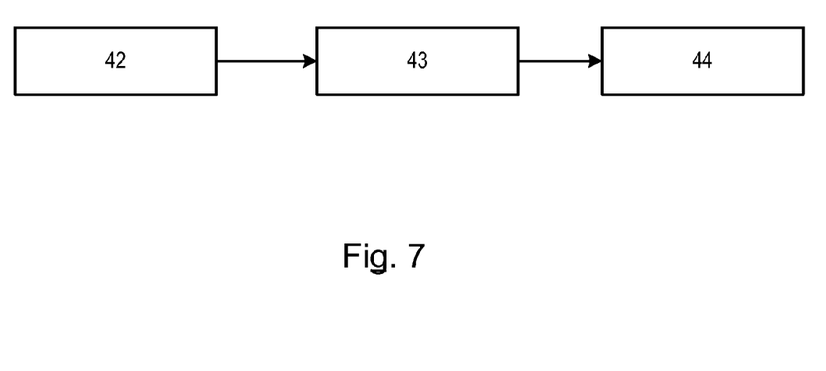
FIG. 7 is flow diagram for a signal scattering analysis technique for detecting reflective properties of the road.

With respect to the second scenario where wet/snow surface lidar signal scattering is increased, this visual effect can be detected by using signal processing and machine learning techniques. FIG. 7 represents a block diagram of an algorithmic flow to perform an analysis for signal scattering.

Figure 8:
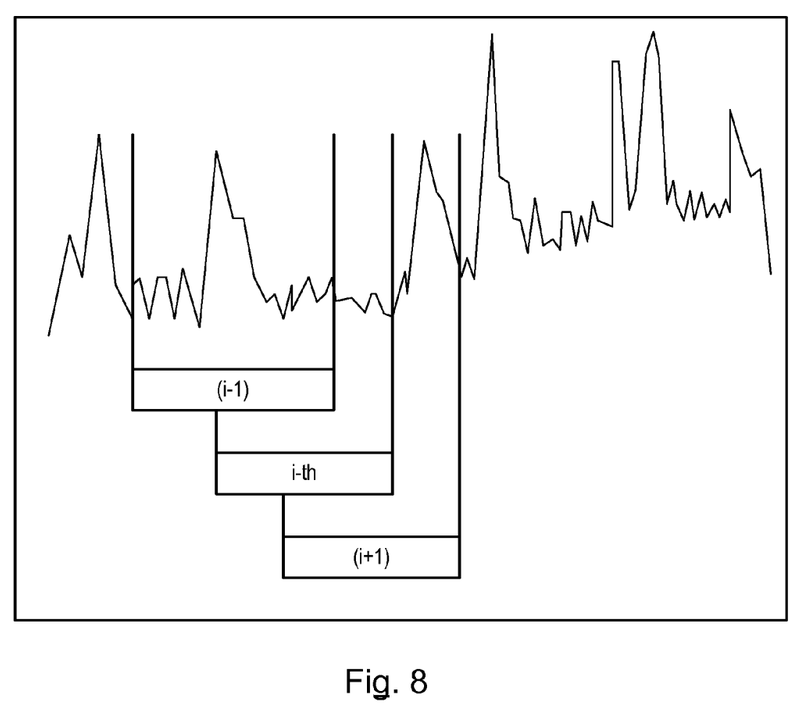
FIG. 8 graphic illustration of a sliding window feature extraction technique.

In block 42, a first signal is scanned by the sliding window and features are extracted per window. A first signal is scanned by a sliding window and features are extracted per window. FIG. 8 illustrates the sliding window. In FIG. 8, a respective window is analyzed at the i–1 window. The window is moved and a next window is analyzed, (ith window). Successive windows are analyzed (i+1 window).

In block 43, features extracted for each window are analyzed. Features that are extracted include, but are not limited to, short signal statistics such as STD or any other statistics measuring deviation from a normal distribution (kurtosis, for example), FFT coefficients and their statistics. In addition, since the sliding window signal is composed of 3D points, principal component analysis (PCA) can be utilized as well as eigenvalues and their ratio for estimating a short window signal scattering.

In addition to FFT, another technique such as a wavelet transform can be used. Wavelet transform is a time-frequency-transformation utilizing a mathematical process for performing signal analysis for a signal frequency that varies over time.

In block 44, the respective features are classified. The last classification step can be applied by any respective classifier including, but not limited to any neural networks, support vector machines (SVM), nearest-neighbor classifiers, etc. Classification labels include, but are not limited to, wet regions, icy regions, dry regions, and snow regions. The feature extraction and classification steps may be combined into one step using deep neural networks technique.

Figure 9A:
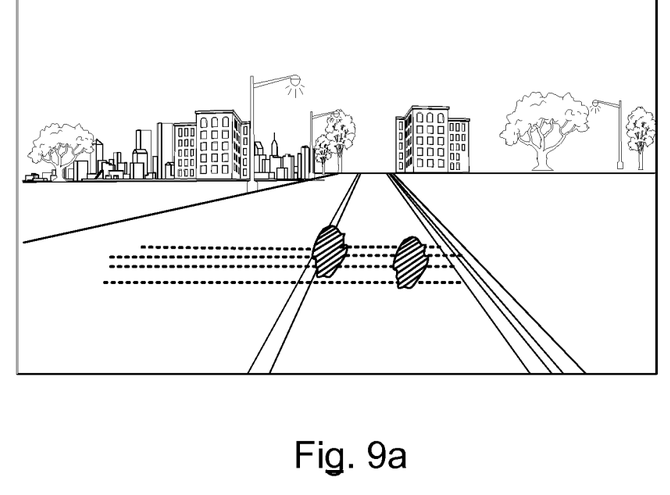
FIGS. 9a and 9b lidar return signals relating the scatting effect of the lidar beam.
Figure 9B:
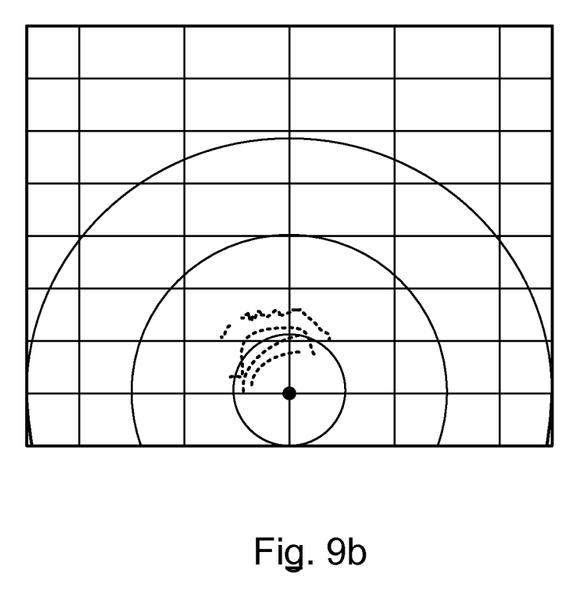

FIGS. 9*a* and 9*b* illustrate lidar return signals relating the scatting effect of the lidar beam. As shown in FIG. 9*b*, while return signals are present, the geometric shape of the return signals are scattered. This type of signal is identified using signal processing and the machine learning techniques as indicated above.

In addition, other sensor data (such as cameras, radar, ultrasonic) can be used in cooperation with the lidar system which assists in making cooperative decisions regarding the road surface condition.

Figure 10:
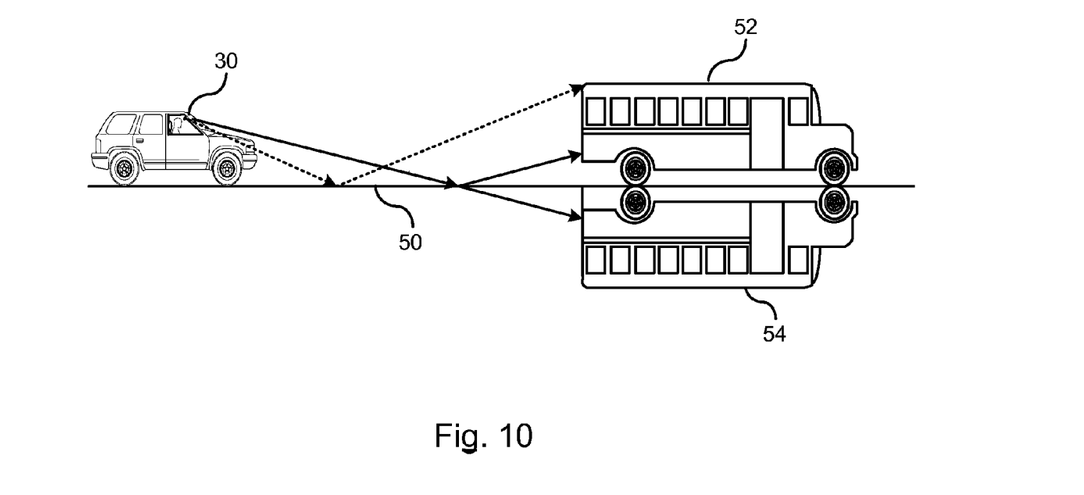
FIG. 10 is a false object detection technique used to identify reflective properties of the road.

FIG. 10 illustrates the third scenario where false objects are detected in the mirrored surface of the road. As shown in FIG. 10, the lidar system transmits a beam of light onto the road of travel 32. Precipitation 50 is present on the road surface. A light reflection on the road surface for the precipitation will have a reflected ray angle that is substantially equal to the incident ray angle. The precipitation 50 on the road of travel functions as a mirror-type surface having reflective properties. After reflection occurs by the mirror surface, the reflected ray hits an object 52 forward of the vehicle. The light bouncing off the front object 52 is returned back and measured by sensor (multi-path) generating secondary echo. This secondary echo returns are 3D points that generates false alarm signals indicating a false/virtual object 54. The false objects are considered virtual points located underground and are projected to the same point under the surface on the virtual object 54 as the real object 52 since real object 52 and the virtual object 54 are substantially the same size; however, it is expected that the intensity of the secondary pulse to be smaller due to multiple reflections.

The process of detecting the false object is described as follows. In step 60, a ground plane is determined utilizing a robust plane fitting technique (RANSAC). A technique such as RANSAC performs ground estimation by shifting and rotating the data to match xy plane and the ground plane.

In step 61, false object points of the virtual object that are located below the ground are identified. The false object points will have an underground point (z<0). This is the same for negative objects such as potholes.

In step 62, false object points from different rays are collected by the lidar system. The different rays collected should be from a substantially same location when projected to the ground. The same is true for a real object, but not for certain characteristics of the road such as potholes.

In step 63, the properties identified in steps 62 and 63 are analyzed in cooperation to identify a false object detection. It is understood that the intersection between the road surface and the false objects correspond to the reflective area of road surface. These respective false object points will coincide with the real lidar points obtained from the first pulses. Detection of false objects further enables reconstruction of real objects by applying symmetry transforms of the false objects from the road surface.

It should be understood that other vehicle subsystems such as a camera based system may be utilized in cooperation with the lidar system for enhancing the probability that a false object below the ground plane is properly detected.

Figure 11A:
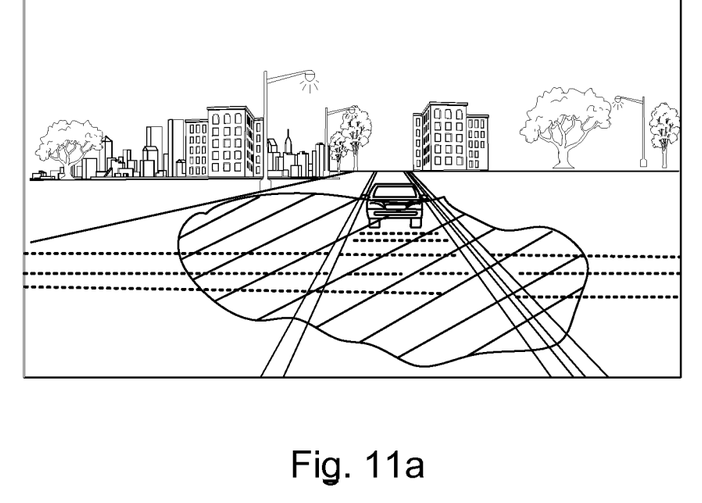
FIGS. 11a and 11b illustrate the lidar return signals indicating false objects.
Figure 11B:
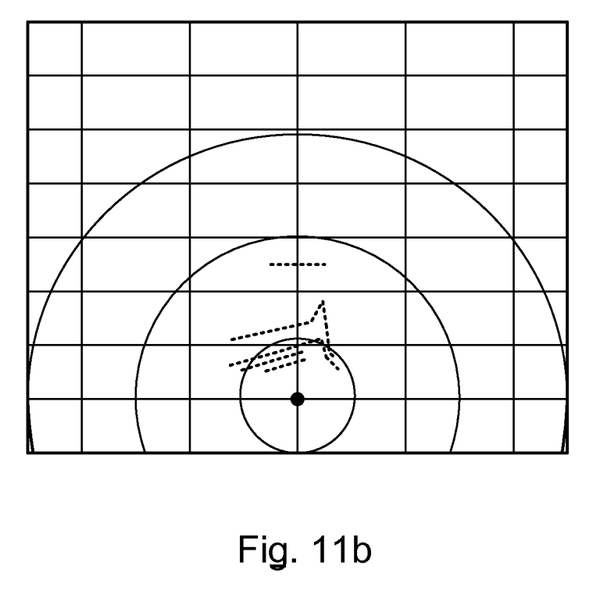

FIGS. 11a and 11b illustrate the lidar return signals for the scenario where false objects are located in the signal. As shown in FIG. 11a, a vehicle 52 is traveling forward of the driven vehicle. Lidar return signals are present; however, respective portions of the return signals are located at a greater distance than expected. In FIG. 11b, a lidar signal return 54 is displaced further from the where the other return signals are present. This indicates that the signal traveled a further distance to bounce off the vehicle 52. Since the other return signals are substantially at a same location in comparison to the return signal 54, a determination is made that the return signal indicates a false object which is indicates that a mirror-like surface is present.

The proposed techniques described herein can be used in embodiments other than vehicle applications for determining separation between objects and backgrounds having different reflectivity, such as usage of lidar for a ship detection at sea. It is understood that the above techniques are not limited to automotive applications, but may be utilized in non-automotive applications.

Moreover, lidar scans can be combined into dense point clouds (if ego-motions sensors are available or from which ego-motion can be estimated) and the same analysis can be applied to point cloud patches, which will provide full information about the road surface surrounding the vehicle.

While certain embodiments of the present invention have been described in detail, those familiar with the art to which this invention relates will recognize various alternative designs and embodiments for practicing the invention as defined by the following claims.

What is claimed is:

1. A method of determining a surface condition of a road of travel, the method comprising the steps of:
    transmitting a light beam directed at a surface in the road of travel utilizing a lidar system;
    analyzing a response at a photodetector of the lidar system after transmitting the light beam;
    determining whether a form of precipitation is present on the road of travel in response to analyzing the response at the photodetector;
    generating a precipitation indicating signal in response to the determination that the ground surface includes a form of precipitation on the road of travel, the precipitation indicating signal provided to an output device to enable stability control functionality.

2. The method of claim 1 wherein analyzing a response at the photodetector includes determining whether a reflective signal is received at the photodetector, wherein no reflective signal received by the photodetector indicates that the form of precipitation is present on the road of travel.

3. The method of claim 2 wherein a secondary sensing device is utilized in cooperation with the lidar system for increasing a probability of determining precipitation on the surface of the road.

4. The method of claim 3 wherein the secondary sensing device determines a type of precipitation on the surface of the road.

5. The method of claim 1 wherein the response includes light signals received at the photodetector, wherein the scattering of the light signals is increased for the received response in comparison to an expected reflective signal where precipitation is present.

6. The method of claim 5 wherein determining whether a scattering of the light signal is present comprises the steps of:
    applying a sliding window to a reflected signal received by the photodetector;
    applying a feature extraction technique to each respective window of the received reflected signal;
    identifying whether a scattering is present within the reflected signal in response to analyzing the extracted features from each respective window.

7. The method of claim 6 wherein the feature extraction technique includes short signal statistics.

8. The method of claim 6 wherein the feature extraction technique includes a standard deviation.

9. The method of claim 6 wherein the feature extraction technique includes Fast Fourier Transforms coefficients.

10. The method of claim 6 wherein the feature extraction technique includes a wavelet transforms technique.

11. The method of claim 6 wherein the feature extraction technique includes principal component analysis.

12. The method of claim 6 wherein a secondary sensing device is utilized in cooperation with the lidar system for increasing a probability of determining precipitation on the surface of the road.

13. The method of claim 12 wherein the secondary sensing device determines a type of precipitation on the surface of the road.

14. The method of claim 5 wherein a classifier is applied to the extracted features identifying the road surface condition.

15. The method of claim 1 wherein analyzing a response at the photodetector includes determining whether a false object is present in a reflective surface on the road of travel.

16. The method of claim 15 wherein the false object are analyzed as objects located beneath the surface of the road based on distance that extends beyond a distance to an intersection of the light beam and the surface of the road.

17. The method of claim 15 wherein the distance to the false object outside of a predetermined threshold of an expected distance to the surface of the road.

18. The method of claim 15 wherein analyzing a response at the photodetector includes determining whether a false object is present in a reflective surface on the road of travel comprises the steps of:

identifying a ground plane using a plane fitting;

identifying false object points located below the surface of the road;

collecting false object points from a plurality of reflected rays received by the photodetector, the plurality of reflected rays intersecting the surface of the road is at a substantially same location of the road surface.

19. The method of claim 18 wherein a secondary sensing device is utilized in cooperation with the lidar system for increasing a probability of determining precipitation on the surface of the road.

20. The method of claim 19 wherein the secondary sensing device determines a type of precipitation on the surface of the road.

* * * * *